United States Patent [19]

Evans et al.

[11] Patent Number: 5,026,826
[45] Date of Patent: Jun. 25, 1991

[54] HUMAN NEUTROPHILIC GRANULOCYTE END-STAGE MATURATION FACTOR AND ITS PREPARATION AND USE

[75] Inventors: Warren H. Evans, Kensington, Md.; Shirley M. Wilson, Washington, D.C.

[73] Assignee: The United States of America as represented by the Secretary of the Department of Health and Human Services, Washington, D.C.

[21] Appl. No.: 273,569

[22] Filed: Nov. 21, 1988

[51] Int. Cl.$^5$ .................... C07K 15/00; A61K 37/02
[52] U.S. Cl. .................... 530/351; 530/350; 530/395; 530/829; 530/838; 424/85.1; 514/8; 514/12; 514/21; 435/701; 435/240.2
[58] Field of Search ............... 530/351, 350, 395, 829, 530/838; 424/424, 85.1; 435/240.2, 70.1; 514/8, 12, 21

[56] References Cited

U.S. PATENT DOCUMENTS 4,504,586 3/1985 Nicolson .................... 435/68
4,658,018 4/1987 Urdal et al. .................... 530/351

OTHER PUBLICATIONS

Choudhury et al., *J. Lab. Clin. Med.*, 1989, vol. 114, pp. 382–388.
Choudhury J. Lab. Clin. Med., 1989, vol. 114, 378–81.
Lymphokine Research Sixth Inter. Lymphokine Workshop Oct. 23–27, 1988, Evian Frand, pp. 285–92, vol. 7(3).
Gabrilove et al., Blood 66, 1985, pp. 407–415.
Lotem et al., *Inter. J. Cancer*, 41, 1988, pp. 101–07.
Leung et al., *PNAS*, 82, 1985, pp. 1209–13.
Motoyoshi et al., Blood, 1978, vol. 52, pp. 1012–1020.
Zsebo et al., *Immunobiol*, 172, 1986, pp. 175–184.
Tomida et al., *FEBS*, 207, 1986, pp. 271–275.
Jyonouchi et al., J. Immunol. 135, 1985, pp. 1891–1899.
Metcalf, Blood, vol. 67, 1986, pp. 251–268.
D. Metcalf, J. of Cellular Physiology Supplement, 1:175–183, (1982).
Motoo Hozumi, Advances in Cancer Research, vol. 38, pp. 121–169, (1983).
Leo Sachs, Science, vol. 238, pp. 1374–1379, (1987).
Eitan Fibach et al., J. Cell. Physiol., vol. 83, 177–186, (1974).
J. Lotem et al., Int. J. Cancer, vol. 25, pp. 763–771, (1980).
A. Burgess et al., Int. J. Cancer, vol. 26, pp. 647–654, (1980).
M. Moore, Journal of Cellular Physiology Supplement 1:53–64, (1982).

*Primary Examiner*—Garnette D. Draper
*Attorney, Agent, or Firm*—Birch, Stewart, Kolasch & Birch

[57] ABSTRACT

A purified inhibitor free human neutrophilic granulocyte end-stage maturation factor (GMF) inhibitor-free human neutrophilic granulocyte end-stage maturation factor is disclosed. The GMF is distinct from granulocyte colony stimulating factor (G-CSF) in both physical and biological properties.

6 Claims, 8 Drawing Sheets

HUMAN NEUTROPHILIC GRANULOCYTE END-STAGE MATURATION FACTOR AND ITS PREPARATION AND USE

BACKGROUND OF THE INVENTION

The production of neutrophilic granulocytic leukocytes in the bone marrow involves a process by which immature progenitor cells committed to the granulocytic line of development undergo proliferation to produce morphologically recognizable precursor cells. The latter further undergo a final phase of nuclear and cytoplasmic maturation which ultimately leads to a highly differentiated, non-dividing, end-stage granulocyte that eventually leaves the marrow and circulates in the blood. Although considerable information has been obtained in recent years about the specific factors that regulate the proliferation of granulocyte progenitor cells,[1] much less is known about the factors that regulate the maturation of the recognizable granulocyte precursor cells.

Using a liquid culture assay system, we showed previously that the end-stage of neutrophilic granulocyte precursors obtained from guinea pig bone marrow could be induced in vitro by dialyzed normal guinea pig serum.[2] We also showed that this maturation-inducing activity could be attributed to the transferrin fraction of this serum and that purified human serum transferrin could be substituted for guinea pig transferrin as a maturation inducer for guinea pig cells.[3]

SUMMARY OF THE INVENTION

In the present study, we have used this assay system to investigate the effects of both dialyzed normal human serum and protein fractions of normal human serum on the end-stage maturation of human granulocyte precursors. Our studies indicate that dialyzed human serum contains a granulocyte maturation factor (GMF) that is distinct from purified human transferrin. The latter does potentiate the effect of GMF on granulocyte precursor maturation, however. We also find that addition of human recombinant granulocyte colony-stimulating factor (r-G-CSF) fails to induce the end-stage maturation of human granulocyte precursors in this assay system.

The present invention is therefore directed to an inhibitor-free human neutrophilic granulocyte end-stage maturation factor. GMF is present in human blood together with an inhibitor which inhibits its neutrophilic granulocyte end-stage maturation activity. Thus, in order to have useful human GMF at least some and preferably substantially all of the inhibitor should be removed. Therefore, "inhibitor free" means that enough of the inhibitor has been removed to allow the human GMF to be used to stimulate human neutrophilic granulocyte end-stage maturation.

The purified human neutrophilic granulocyte end-stage maturation factor preferably has the following characteristics (1) promotes maturation of neutrophilic granulocyte precursors to form end-stage neutrophilic granulocytes; (2) is substantially free of non-specific proteins; (3) is capable of inducing human neutrophilic granulocytes to produce alkaline phosphatase; (4) the human neutrophilic granulocyte maturation effect can be potentiated by purified human transferrin; (5) does not substantially promote proliferation of human granulocyte precursors in a liquid culture; (6) is inactivated by treatment with protease; (7) binds tightly at pH 7 to a DEAE Fractogel chromatographic column; and (8) elutes from a size exclusion HPLC column in the molecular weight range of an albumin standard having a molecular weight of about 65,000 daltons.

The maturation factor of the present invention has potential utility in its purified form in research on the biochemical mechanisms involved in the regulation of human granulocyte maturation under normal and pathological conditions. This regulatory protein, when purified, could be useful in treating human diseases involving defects in neutrophilic granulocyte end-stage maturation such as in the acute and chronic myeloid leukemias. This factor could also be useful in stimulating granulocyte maturation in patients who receive bone marrow transplants to replace marrow cells destroyed by X-irradiation and/or chemotherapy. The GMF is potentially useful in the treatment of any conditions or diseases which result in a low white blood cell count (pancytopenia) such as acquired immune deficiency syndrome (A.I.D.S.) or burn victims.

The present invention is therefore also directed to a method for stimulating human end-stage maturation which comprises contacting the maturation factor with human neutrophilic granulocytes. In clinical use the method would comprise administering the maturation factor to a patient deficient in granulocyte end-stage maturation.

It is contemplated that the mode of administration and dosages of the GMF will be about the same as that for human granulocyte colony stimulating factor. A preferred mode of administration would be intravenous (i.v.) administration at a dose of about $5 \times 10^4$ to $3 \times 10^6$ Units per kg of body weight per day, preferably about $1.5 \times 10^6$ Units per kg of body weight per day. Intravenous administration is preferred because i.v. administration would be the best way to deliver the GMF to the desired bone marrow. Intraperatoneal (i.p.) or subcutaneous (s.c.) injection are also possible modes of administration.

50 Units of GMF equals the amount of GMF required to produce one-half (50%) of the maximal obtainable maturation activity in a dose response assay. The maximal obtainable activity is the maximum increase in the number of mature cells, i.e., the number of mature cells after treatment minus the number of cells if no treatment is given. 50 Units of GMF therefore equals the amount of GMF necessary to increase the number of mature cells by one-half of the maximum obtainable in the dose response assay.

GMF is apparently present in human blood in a concentration of about 50,000 Units/ml (together with a maturation inhibitor). Thus, when GMF is used for therapy, it may be useful to attempt to restore the GMF to approximately this level. This can be accomplished by administering the GMF together with an injectable non-toxic pharmaceutical carrier in an amount substantially higher than 50,000 U/ml. The actual concentration of the GMF in the injectable composition will vary depending upon dose selected and the volume of the injection. It is anticipated that continuous i.v. administration by use of a central venous catheter may be useful. Thus, the concentration of GMF in the i.v. solution may range from $1.25 \times 10^3$ to $7.5 \times 10^4$ Units per ml based on a 25 kg adult receiving 1,000 ml of i.v solution over a 24 hour period. Any conventional injectable carriers are acceptable as long as they are non-toxic and contain no GMF inhibitors. Preferably, the GMF should be soluble in the liquid carrier, however, the injectable solution may be an emulsion of GMF and one or more solvents and/or emulsifying agents. An example of a potentially useful i.v. solution would be a sterile 0.45% saline solution containing 5% dextrose.

The present invention is also directed to a method for removing or separating a human neutrophilic granulocyte end-stage maturation factor inhibitor from a solution which comprises contacting the solution with a material capable of hydrophobically interacting with the inhibitor to bind the inhibitor. More specifically, the method comprises the step of passing human blood serum containing human granulocyte end-stage maturation factor and an inhibitor thereof, through a column packed with a polymer having hydrophobic groups which selectively bind the inhibitor and not the maturation factor to separate the inhibitor from the maturation factor.

It is believed that the inhibitor is selectively bound to a material by hydrophobic interaction with the material. A preferred material is DEAE Fractogel (distributed by E. M. Reagents, Inc., manufactured by MCB Mfg. Inc., associate of E. Merck, Darmstadt, Germany) which is a starch/polyvinyl material. It is believed that vinyl groups contained in the material serve as hydrophobic groups to selectively bind the inhibitor but not the maturation factor. Another material which may be useful is Phenyl Sepharose (Pharmacia, Upsula, Sweden). The phenyl groups on the Sepharose may function as hydrophobic groups to selectively bind the inhibitor. Various polymers having hydrophobic groups such as aliphatic, aromatic, vinyl, etc. may be useful as the hydrophobic interaction material. The material is preferably packed in a column and the serum is passed through the material packed in the column whereby the inhibitor binds to the material by hydrophobic interaction.

DETAILED DESCRIPTION OF THE INVENTION MATERIALS AND METHODS

Bone marrow cell and serum preparation

Figure 1:
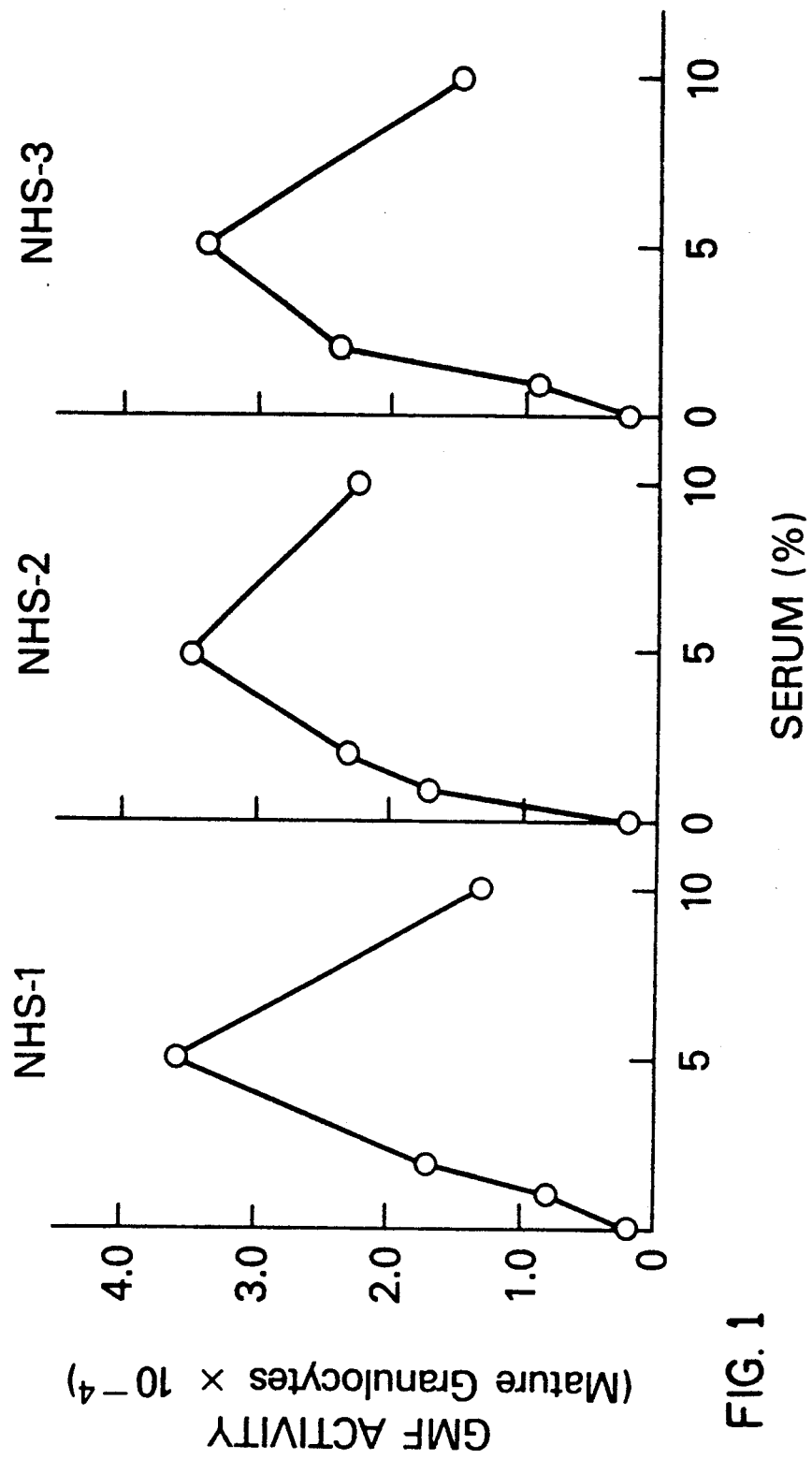
FIG. 1. Dose response effect of dialyzed normal human sera from three different individuals (NHS-1, NHS-2, NHS-3) on human granulocyte maturation in vitro. GMF activity is expressed as the number of mature granulocytes produced per $10^5$ starting granulocyte precursors.

All bone marrow and serum samples were obtained from healthy human donors. Sterile technique was used throughout this study for processing marrow and serum samples.

Bone marrow cells were withdrawn from the posterior iliac crest, collected in Dulbecco's phosphate-buffered saline (Quality Biological, Inc., Gaithersburg, Md.) and enriched in immature granulocytes by Ficoll density centrifugation as described previously,[4] except that after centrifugation only the top 20 ml of the Ficoll supernatant fraction was removed to avoid contamination by the more mature granulocytes present in the bottom 5 ml of supernatant fraction. The enriched granulocyte precursor fraction consisted of the following distribution of cell types (values expressed as the mean ±SD, n=4): 60±3% myeloblasts plus promyelocytes, 25±4% myelocytes plus metamyelocytes, 1±1% mature neutrophilic granulocytes, 3±2% macrophages, 5±3% lymphocytes and 6±2% other non-granulocytes chiefly eosinophils and erythrocyte precursors.

All serum samples were stored at $-75°$ C. until ready for use. Before addition to cell cultures, all sera were dialyzed for 24 hours against 50 volumes of 0.15M NaCl, with one change of the dialysis medium after 6 hours.

Cell culture procedure and maturation assays

Incubation of granulocyte precursor cells in liquid cultures was carried out in 96-well tissue culture clusters with flat bottom wells (Costar, Cambridge, Mass.) as described previously.[3] Briefly, $4.0 \times 10^5$ immature bone marrow cells were placed in 0.2 ml RPMI-1640 medium (Whittaker M. A. Bioproducts, Inc. Walkersville, Md.) supplemented with penicillin (100 units/ml), streptomycin (100 μg/ml), sodium pyruvate (1.0 mM) and zinc sulfate (0.01 mM) and containing various serum protein fractions or regulatory proteins as indicated. Highly purified human transferrin added to some cultures was prepared by a method described in detail previously,[31] or was obtained from Cappel-Cooper Biomedicals, Inc., Malvern, Pa. Human recombinant granulocyte colony stimulating factor (r-G-CSF), having a specific activity of $2 \times 10^8$ units/mg protein prior to formulation in human serum albumin (0.025%), was a product of Amgen Biologicals, Thousand Oaks, Calif. The same human serum albumin solution (0.025%) used to formulate the r-G-CSF served as a control in maturation assays employing this factor.

The cell cultures were incubated for 6 days at 37° C. in a humidified atmosphere containing 95% air and 5% $CO_2$. After incubation, the cells were removed quantitatively (recovery >95%) from the wells for morphological and enzymatic analyses. Viability counts using trypan blue exclusion showed that >95% of the starting cells were viable, and incubated cells were between 90–95% viable.

For the determination of morphological maturation, suitable aliquots of the culture suspension were used for total and differential cell counts as previously described.[4] Neutrophilic granulocytes were classed as mature cells (polymorphonuclears and bands) and as precursor cells (metamyelocytes, myelocytes, promyelocytes and blasts). The absolute number of each cell type was obtained by multiplying the percentage of the cell type in the population by the total number of cells in the cell suspension. The morphological assay results are expressed as the number of mature cells produced per $10^5$ starting granulocyte precursors in order to standardize the data and compensate for small variations in the numbers of starting granulocyte precursors among various marrow donors.

The biochemical assay used to detect the presence of alkaline phosphatase activity in mature, end-stage granulocytes has been described in detail previously.[3]

Chromatography

The precautions taken to maintain the sterility of the chromatographic fractions have been described in detail,[3] and using these precautions, we observed no bacterial growth in cultures to which chromatographic fractions of serum were added.

Partial purification of GMF activity from human serum was carried out by ion-exchange displacement chromatography on DEAE-Fractogel according to the method of Peterson et al.[5] Fractogel TSK DEAE-650S (E. M. Science Inc., Gibbstown, N.J.) was packed into a 7-ml column and equilibrated with starting buffer (10 mM sodium phosphate, pH 7.0) at 4° C. Human serum (3 ml) was dialyzed overnight against 17 volumes of starting buffer with one change of the dialysis medium after 6 hours and was then applied to the DEAE-Fractogel column, followed by a 0.9% solution (in starting buffer) of carboxymethyldextran (CM-D) having a reciprocal pellet volume (RPV) value[5] of 7. This displacer solution was then followed by 0.5M NaCl in starting buffer. The flow rate for the entire chromatographic run was 10 ml/hr. Fractions (2.5 ml) were collected and their absorbance at 280 nm was determined. Suitable aliquots of each fraction were also assayed for their ability to induce both end-stage granulocyte morphological maturation and alkaline phosphatase activity in the liquid culture maturation assay system.

Size exclusion high performance liquid chromatography (SE-HPLC) was carried out using the Beckman Instruments Co. (Fullerton, Calif.) solvent metering system, absorbance detector and sample injection valve described previously.[3] The SE-HPLC column consisted of two Bio Sil TSK-250 cartridges (300×7.5 mm, exclusion limit of 300,000 Daltons for globular proteins, Bio-Rad Laboratories, Richmond, Calif.) connected in series and equilibrated at 25° C. with 10 mM sodium phosphate (pH 6.8)–0.1M NaCl. The molecular weight standards (Bio-Rad Laboratories, Richmond, Calif.) used to calibrate the column were as follows: thyroglobulin (MW 760,000), gamma globulin (MW 158,000), ovalbumin (MW 44,000) and Vitamin B-12 (MW 1,350). Purified human transferrin, prepared as described previously,[3] and having a molecular weight of 79,600[6] also served as a reference standard. The partially purified GMF fraction obtained by DEAE-Fractogel chromatography was dialyzed against 10 mM sodium phosphate buffer (pH 6.8)–0.10M NaCl, and 1.0 ml of undiluted serum equivalents of this fraction was applied to the SE-HPLC column, followed by the column running buffer (0.01 M sodium phosphate, pH 6.8–0.1M NaCl) at a flow rate of 1.0 ml/minute. Fractions (1.0 ml) were collected and their absorbance at 280 nm was determined. Suitable aliquots of each fraction were also assayed for GMF activity.

Polyacrylamide gel electrophoresis

Electrophoretic separation of proteins in serum samples and chromatographic fractions was carried out using the sodium dodecyl sulfate (SDS)-polyacrylamide gel system of Laemmli.[7/] Molecular weight standards (Bio-Rad Laboratories, Richmond, Calif.) used to calibrate this electrophoretic system were as follows: lysozyme (MW 14,400), soybean trypsin inhibitor (MW 21,500), carbonic anhydrase (MW 31,000), ovalbumin (MW 43,000), bovine serum albumin (MW 66,200) and phosphorylase B (MW 97,400). Highly purified human transferrin also served as a standard and was prepared as described previously.[3/]

Protease digestion of partially purified GMF

Duplicate aliquots of the active peak fraction from the DEAE-Fractogel column, each containing 1 mg of protein, were incubated for 4 hours at 37° C. in 10 mM sodium phosphate buffer (pH 7.0) containing 0.5M NaCl and 1.25 units of insoluble protease activity (from *Streptomyces griseus*, attached either to beaded agarose or to carboxymethyl cellulose, supplied by Sigma Chem. Co., St. Louis, Mo., and washed with sterile distilled $H_2O$ to remove borate salts). Samples incubated with heat-inactivated (100° C., 60 minutes) insoluble protease samples served as controls. After incubation the samples were centrifuged at 1000 g for 10 minutes and the supernatant fluid was assayed for GMF activity.

Protein determination

The protein content of serum and serum fractions was determined by the method of Lowry et al.[8/]

RESULTS

Effect of normal human serum on end-stage maturation of human granulocyte precursors As a first step towards answering the question as to whether the end-stage morphological maturation of human granulocyte precursors in liquid culture was dependent on a regulatory protein present in normal human serum, the effect of varying the concentration of human serum in the culture medium over a range of 0% to 10% was studied. FIG. 1 shows the results obtained with sera from three different normal human donors. All three dialyzed sera produced an increasing stimulatory effect on granulocyte end-stage maturation which reached a maximum at 5% serum. At this serum dose, 20-25% of the cells in the culture were mature end-stage granulocytes, representing about a 12-fold increase in the number of these cells relative to the number of these cells in the starting cell suspension. Granulocyte precursor cells decreased in number to about 30% of starting levels. The mature cells produced in these cultures were indistinguishable morphologically from their counterparts produced in vivo and were identical in appearance to such cells produced in vitro in the presence of partially purified preparations of GMF obtained from human serum (as shown below in FIG. 5B). At a serum dose of 10%, all three sera showed a pronounced decrease in the maturation-inducing activity relative to the 5% serum dose. These findings indicate that human serum contains both stimulating and inhibitory factors that regulate the end-stage maturation of human granulocyte precursors in this liquid culture maturation assay system.

Effect of transferrin and of human recombinant colony-stimulating factor on granulocyte end-stage maturation In order to determine which of the many non-dialyzable factors in serum might be responsible for the observed granulocyte maturation-inducing activity of dialyzed human serum, we first tested the effect of purified human transferrin in the maturation assay since we showed previously that this protein could substitute for guinea pig transferrin as a maturation-inducer for guinea granulocyte precursors. The effect of human recombinant granulocyte colony-stimulating factor (r-G-CSF) was also studied, using a range of concentrations (50-500 units/ml) for this factor that is known to support the growth of human granulocyte colonies in semisolid cultures.[9/] The results, shown in Table 1, indicate that neither human transferrin nor human r-G-CSF can substitute for dialyzed serum as a granulocyte maturation-inducing factor in this liquid culture maturation assay system. Adding human transferrin at a concentration of 125 µg/ml to cultures containing the various doses of r-G-CSF shown in Table 1 also failed to induce granulocyte maturation in these assays (data not shown).

TABLE 1

Effect of Human Serum, Transferrin and Recombinant Granulocyte Colony-Stimulating Factor on Human Granulocyte End-Stage Maturation In Vitro

| Addition To Culture | GMF Activity (Mature Granulocyte $\times 10^{-4}$) |
|---|---|
| None | 0.0 ± 0.0 |
| Human Serum (5.0%) | 3.7 ± 0.4 |
| Human Transferrin (65 µg/ml) | 0.0 ± 0.0 |
| Human Transferrin (130 µg/ml) | 0.0 ± 0.0 |
| Human Transferrin (260 µg/ml) | 0.0 ± 0.0 |
| Human r-G-CSF (50 units/ml) | 0.0 ± 0.0 |
| Human r-G-CSF (100 units/ml) | 0.0 ± 0.0 |
| Human r-G-CSF (500 units/ml) | 0.0 ± 0.0 |

Cell culture-conditions are as described in Materials and Methods. Purified human transferrin was obtained from Cappel-Cooper Biomedical, Inc. (Note: similar results were obtained with human transferrin prepared in our laboratory as described[3]). Human r-G-CSF was a product of Amgen Biologicals. Results are the mean of two determinations using granulocyte precursor cells from two different bone marrow donors and are expressed as the number of mature granulocytes produced per $10^5$ starting granulocyte precursors.

Figure 2:
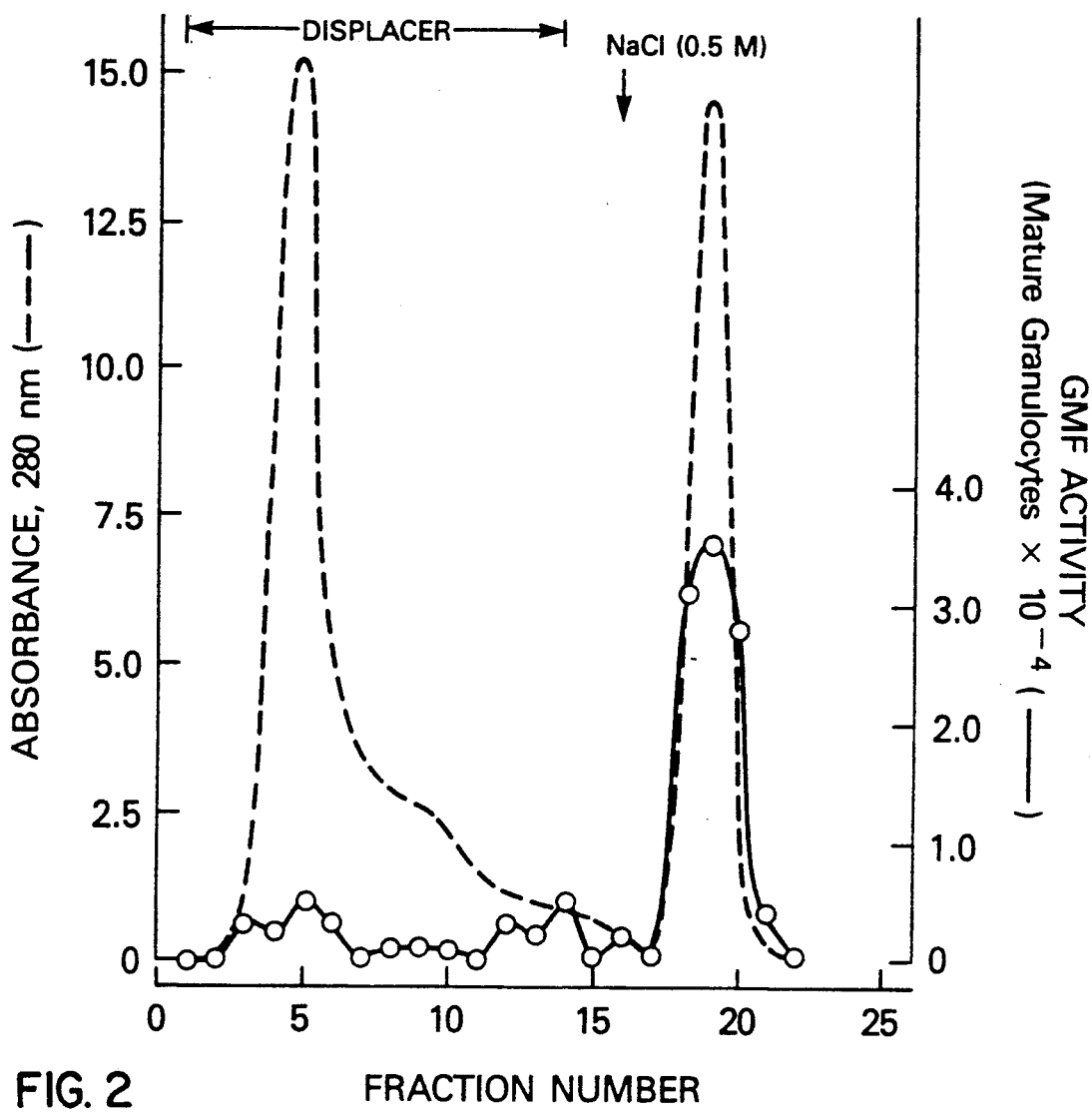
FIG. 2. Fractionation of normal human serum GMF by DEAE-Fractogel 650S displacement chromatography. A 3-ml sample of serum dialyzed against starting buffer (10 mM sodium phosphate buffer pH 7.0) was applied to the column and eluted with CM-D displacer solution, followed by 0.5M NaCl, as indicated in the graph and as described in Materials and Methods. Fractions (2.5 ml) were collected and their absorbance profile at 280 nm (—) was determined. Suitable aliquots of the fractions were also assayed for GMF activity as described in Materials and Methods. GMF activity is expressed as the number of mature granulocytes produced per $10^5$ starting granulocyte precursors. The results are typical of three determinations made on sera from three different human donors.
Figure 3:
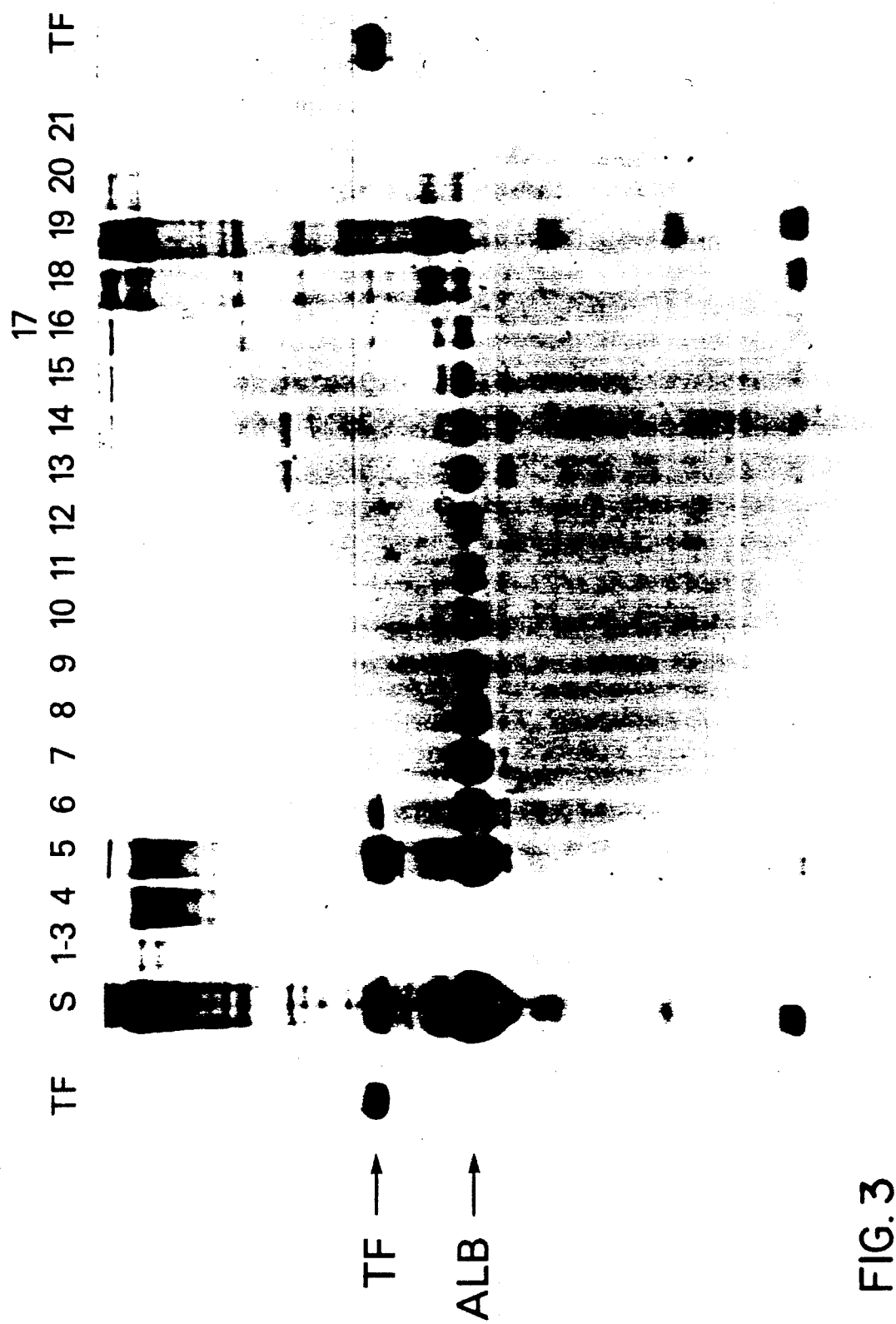
FIG. 3. Laemmli SDS-polyacrylamide gel electrophoresis of DEAE-Fractogel chromatography fractions of human serum containing GMF. Aliquots of all fractions (1-21) applied to the gel were equivalent to 1.0 µl of undiluted starting serum (S). Transferrin (TF), prepared as described in Materials and Methods served as a reference standard and was applied to the gel in an amount (2.5 µg) approximately equal to that present in the starting serum sample (S). All samples were run under non-reducing conditions and migration is downward toward the positive electrode. The gel is stained with Coomassie blue and the arrows indicate the location of the transferrin (TF) and albumin (ALB) bands in the starting serum sample (S).

Properties of a partially purified preparation of GMF obtained by DEAE-Fractogel chromatoqraphy of human serum FIG. 2 shows a chromatographic profile of GMF obtained when human serum, dialyzed against 10 mM phosphate buffer, pH 7.0, was applied to a column of DEAE-Fractogel and the proteins were displaced from the column by CM-D displacers, followed by step elution with 0.5M NaCl. FIG. 3 shows the Laemmli SDS-gel electrophoretic profiles of successive chromatographic protein fractions obtained from the DEAE-Fractogel column. These results are typical of those obtained with three different human sera. GMF was found primarily associated with the tightly bound (i.e. more negatively charged) protein fraction that was eluted with 0.5M NaCl (see FIG. 2, fractions 18, 19, 20) and contained approximately 17% of the starting serum protein. It should be noted that almost all of the serum transferrin was present in fraction 5 (see FIG. 3) which was essentially devoid of GMF activity. We find that this partially purified GMF can be stored for up to 6 months at −75° C. without appreciable loss of activity. GMF activity in this fraction was completely destroyed when exposed to insoluble protease, as described under Methods, supporting the assumption that GMF activity resides in a protein molecule.

Figure 4:
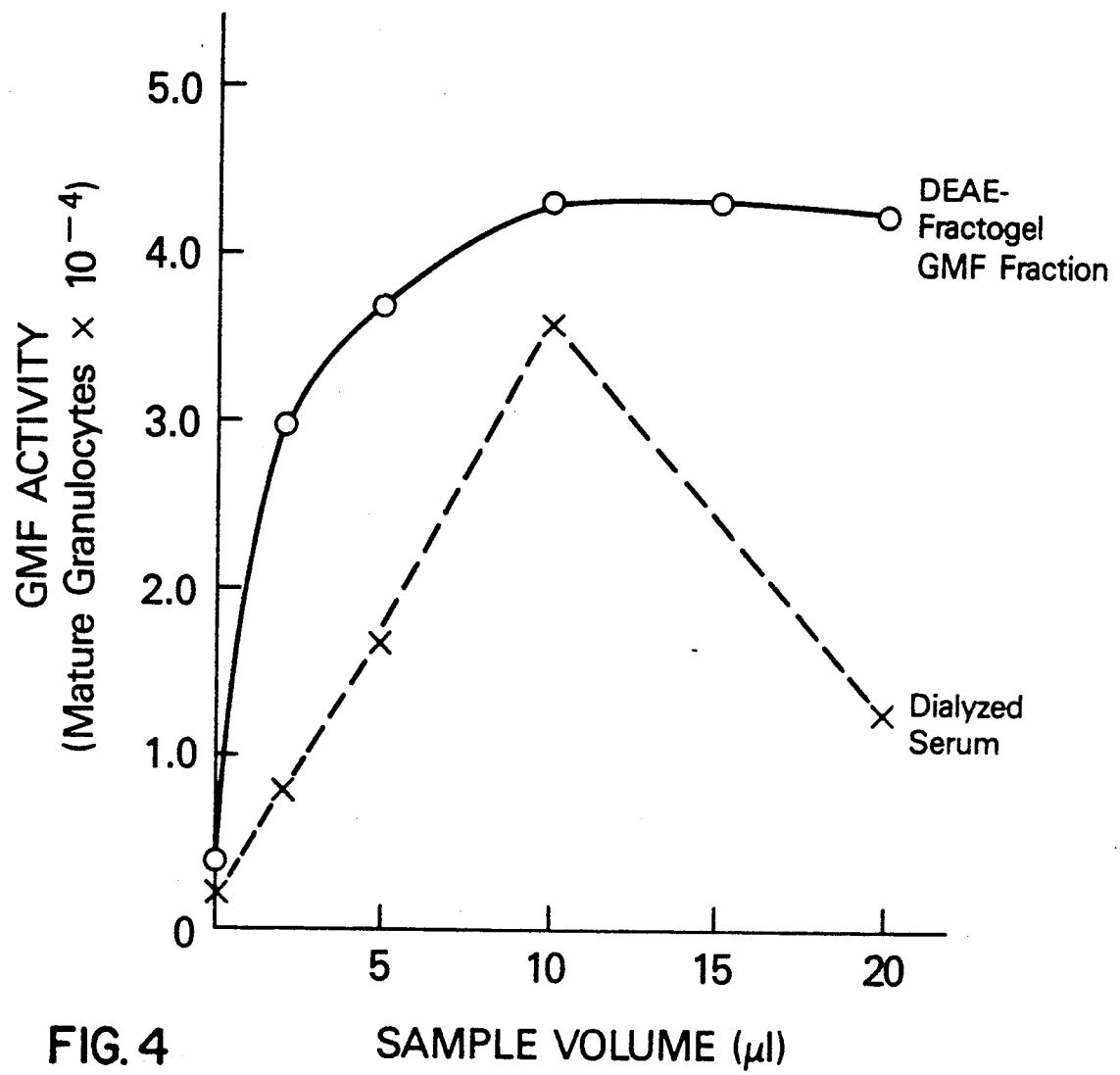
FIG. 4. Dose response effect of the DEAE-Fractogel GMF fraction on human granulocyte maturation in vitro. Cell culture conditions are as described in Materials and Methods. The dose response curve for dialyzed human serum (—) is also shown for comparison with that of partially purified GMF (-0-). The sample volumes are expressed as microliters of undiluted serum for dialyzed serum or as undiluted serum equivalents for the DEAE-Fractogel fraction. GMF activity is expressed as the number of mature granulocytes produced per $10^5$ starting granulocyte precursors. The protein concentrations of the dialyzed serum and the GMF fraction are 67 mg/ml and 9.2 mg/ml, respectively.

The dose response curve for partially purified GMF is shown in FIG. 4 and, for comparison, that for dialyzed human serum is also shown. The results indicate that the maturation response is proportional to the dose of partially purified GMF up to approximately 10 μl of undiluted serum equivalents. Above this dose a saturation limit for the maturation response is reached suggesting that this GMF fraction, unlike dialyzed serum, contains little, if any, maturation inhibitor. The values for total cell counts in cultures showing maximal stimulation of maturation by partially purified GMF after 6 days were 92% of the values for total cell counts in the starting cell cultures indicating that no major increase in total cell number occurred in cultures containing partially purified GMF. This finding suggests that GMF primarily affects the end-stage maturation of human granulocyte precursors and has no measurable effect on their proliferation in this assay system.

Figure 5:
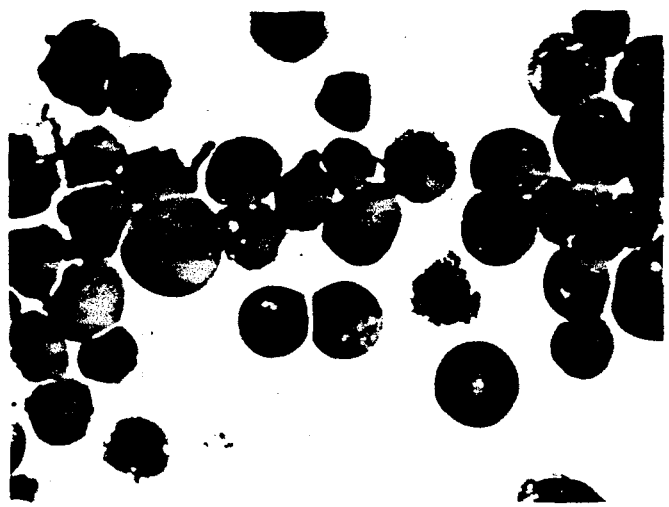
FIG. 5. Photomicrographs of human granulocyte cell populations before and after cell culture in the presence and absence of partially purified GMF. (A) Human granulocyte precursor cells used as starting cells in culture. (B) Mature granulocytes formed after 6-day culture of granulocyte precursors in medium containing partially purified GMF obtained by DEAE-Fractogel chromatography (see chromatograph shown in FIG. 2). (C) Macrophages and lymphocytes present in cultures of granulocyte precursors incubated for 6 days in the absence of added GMF.
Figure 5:
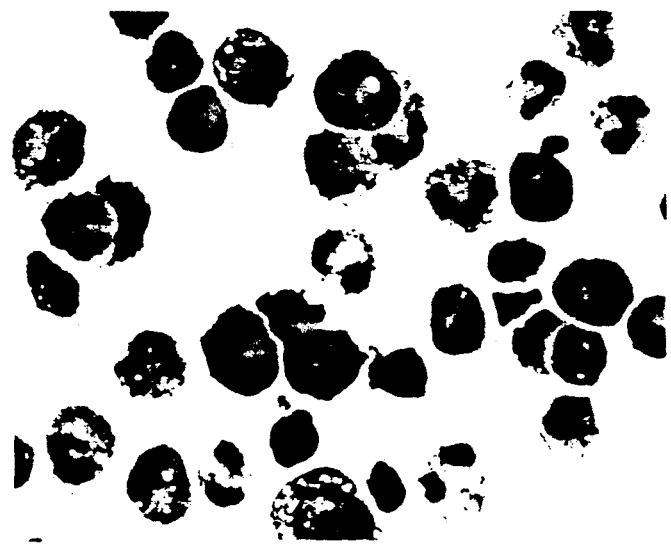
Figure 5:

FIG. 5A shows a typical microscope field of a stained preparation of granulocyte precursors in the starting cell cultures. FIG. 5B shows a typical field of mature granulocytes produced from these precursors after 6 days culture in the presence of 15 μl of serum equivalents of the partially purified GMF. At this dose of GMF approximately 40% of the cells in the culture were mature granulocytes representing about a 19-fold increase in the number of these cells relative to that in the starting cell culture. As with dialyzed serum, the mature cells produced in the cultures with partially purified GMF were indistinguishable from mature granulocytes produced in vivo. FIG. 5C shows a photomicrograph of a typical microscope field of cells harvested from 6-day cultures of granulocyte precursors incubated in the absence of human serum GMF. Few if any mature granulocytes could be detected in such cultures and the cell population typically consisted of macrophages (23%), lymphocytes (58%) and residual immature granulocytes (19%).

Figure 6:
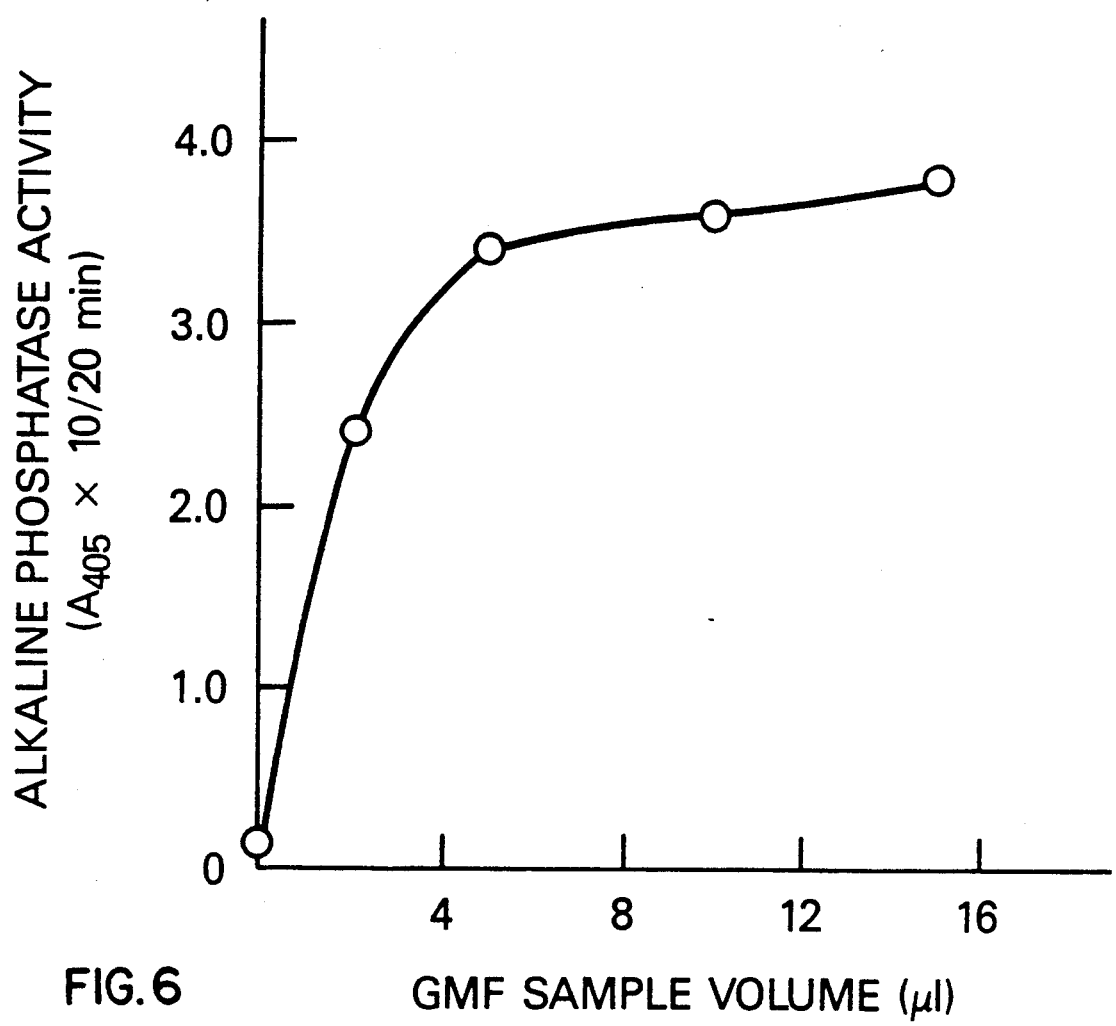
FIG. 6. Dose response effect of the DEAE-Fractogel GMF fraction on human granulocyte alkaline phosphatase induction in vitro. The cell culture conditions are as described in Materials and Methods. The GMF sample volumes are equivalent to corresponding volumes of undiluted human serum. Alkaline phosphatase activity is expressed as the change in absorbance at 405 nm (A405) after 20 min, using p-nitrophenyl phosphate as enzyme substrate (see Materials and Methods).

As another measure of granulocyte maturation in vitro, the dose response curve was also determined for the induction of granulocyte alkaline phosphatase. This enzyme is a specific marker for granulocytes among the various cells in human bone marrow and appears only at the end-stage of maturation of granulocytes in vivo.[10, 11] The results obtained, shown in FIG. 6, are similar to those obtained using the morphological assay for granulocyte maturation (see FIG. 4). These results suggest that GMF is capable of inducing both the morphological and biochemical maturation of human granulocyte precursors in vitro.

Potentiation of GMF activity by purified human transferrin

Figure 7:
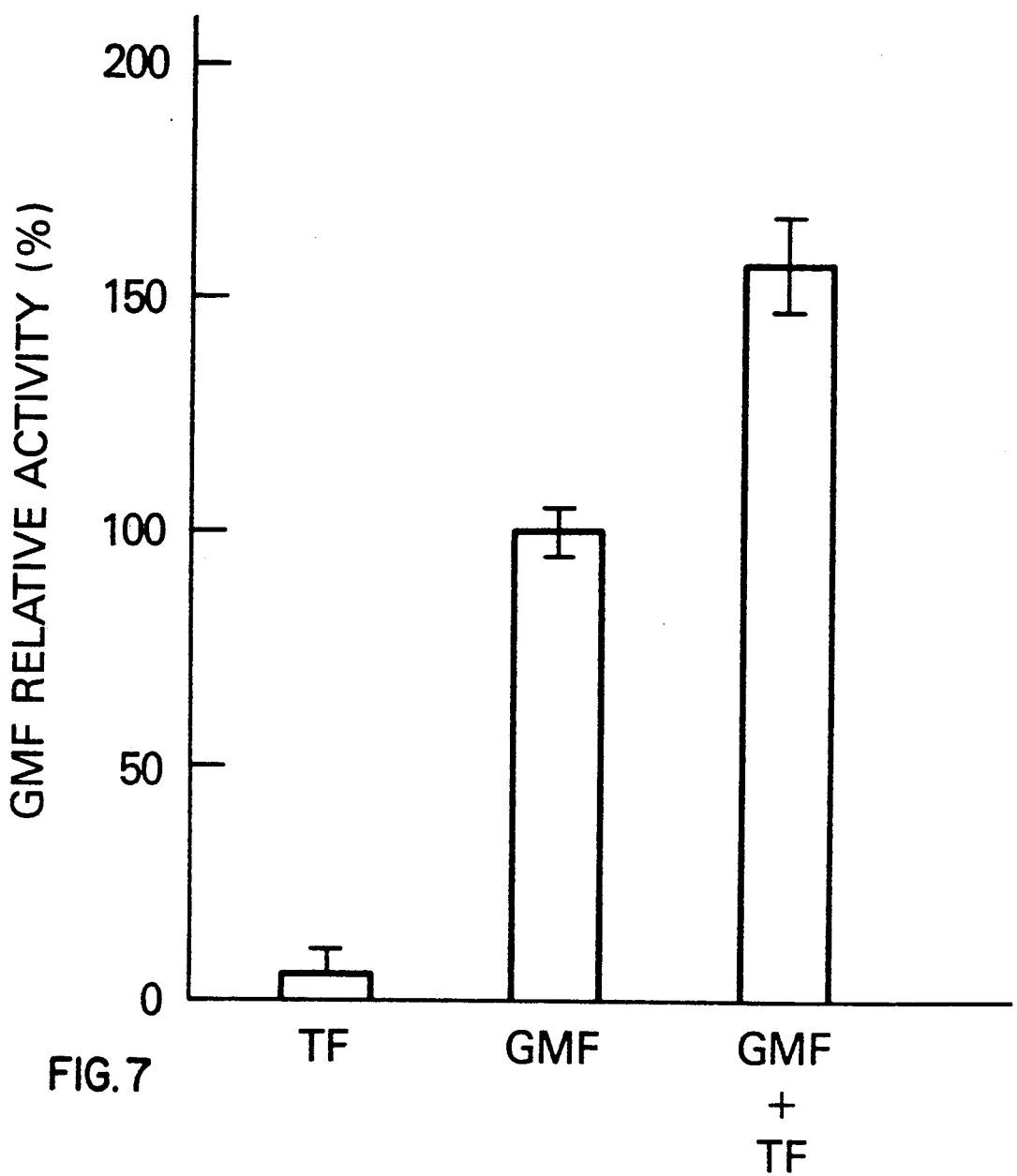
FIG. 7. Potentiation by human transferrin of the effect of partially purified GMF on human granulocyte precursor maturation in vitro. Culture conditions and human transferrin (TF) preparation are as described in Materials and Methods. The concentration of transferrin in the culture medium was 125 µg/ml. Partially purified GMF was obtained by DEAE-Fractogel displacement chromatography as shown in FIG. 2 and was added to the culture medium at a dose of 20 µl of undiluted serum equivalents. GMF activity is expressed as the number of mature granulocytes produced per $10^5$ starting granulocyte precursors. The data shown are the mean of duplicate determinations.

Though we observed no direct effect of transferrin on granulocyte end-stage maturation in this assay system, we investigated the possibility that purified transferrin might serve as a co-factor for granulocyte maturation. The results of this study shown in FIG. 7 indicate that purified transferrin can markedly potentiate the effect of partially purified GMF, since cultures containing GMF plus transferrin showed a 57% increase in maturation response over those containing GMF alone.

Figure 8:
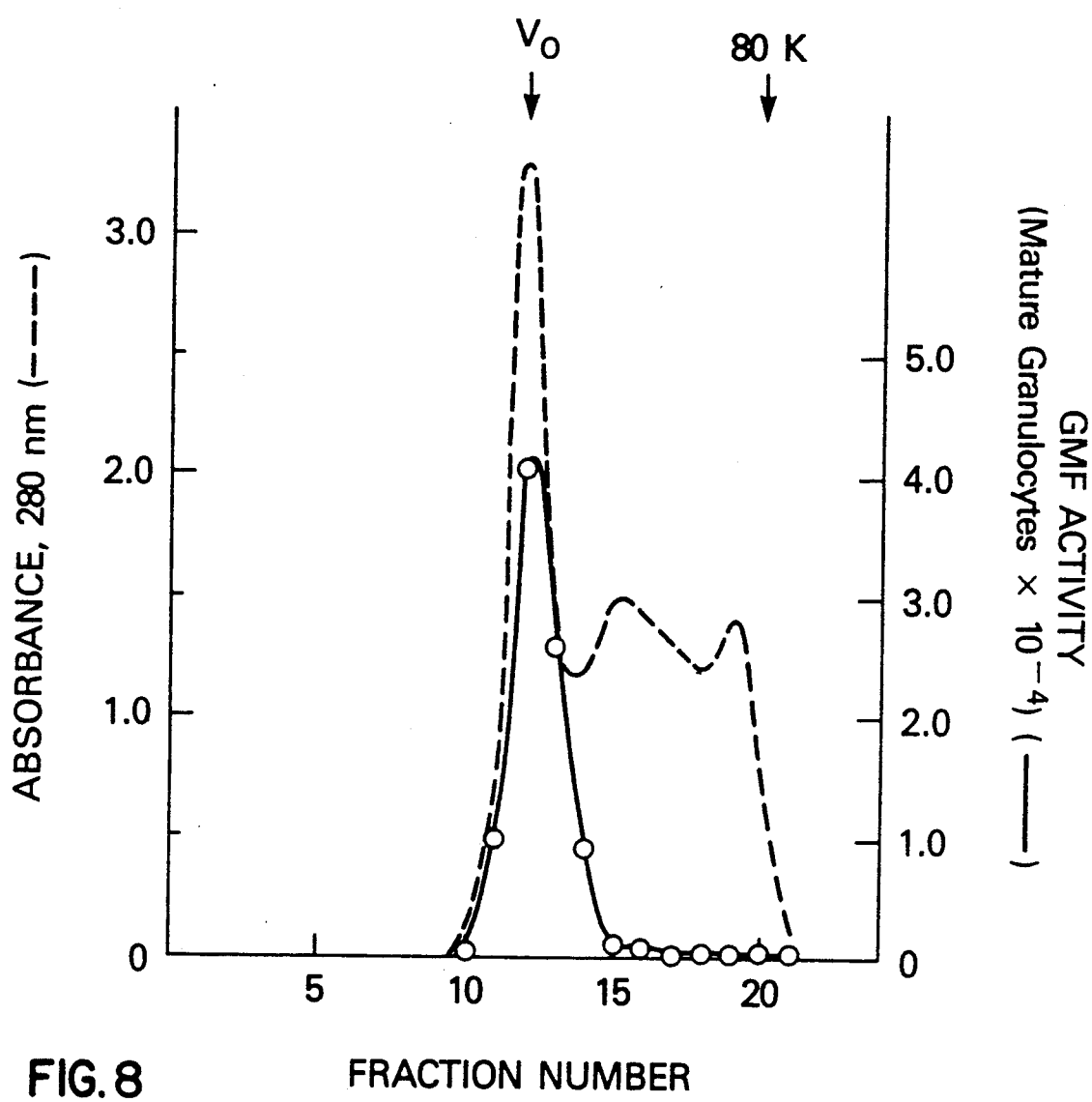
FIG. 8. Fractionation of human serum GMF by size exclusion high performance liquid chromatography (SE-HPLC). The active GMF peak fraction from the DEAE-Fractogel chromatographic step shown in FIG. 2 was dialyzed against the SE-HPLC column equilibration buffer (10 mM sodium phosphate, pH 6.8, 0.1M NaCl) and a portion (1.0 ml) was applied to the SE-HPLC column followed by equilibration buffer. Fractions (1.0 ml, each equivalent to 1.0 ml of undiluted human serum) were collected and their absorbance profile at 280 nm (—) was determined. Suitable aliquots of the fractions were also assayed for GMF activity as described in Materials and Methods. GMF activity is expressed as the number of mature granulocytes produced per $10^5$ starting granulocyte precursors.

Size exclusion high performance liquid chromatography (SE-HPLC) of partially purified GMF Fractionation of the partially purified GMF preparation by SE-HPLC was carried out to determine whether GMF was associated with the excluded or included protein fractions obtained from the SE-HPLC column. As can be seen in FIG. 8, the peak of GMF activity coincided with the void volume of the column which has an upper exclusion limit of 300,000 Daltons. These results do not necessarily imply that GMF has a molecular weight equal to or greater than 300,000 since it is also possible that this activity is associated with a smaller molecule that is bound to some high molecular weight protein present in human serum. We have also found that when normal human serum is chromatographed directly by SE-HPLC, GMF elutes from the column in a molecular weight range of an albumin standard having a molecular weight of 65,000 daltons (data not shown). The data suggests that GMF is capable of forming high molecular weight complexes either with itself or with some other compound in serum.

DISCUSSION

The results obtained in the present study clearly indicate that the conversion of human granulocyte precursors to mature, end-stage granulocytes in vitro is controlled by a regulatory protein that is present in normal human serum. Previously, we showed that the maturation-inducing activity of guinea pig serum for guinea pig bone marrow granulocyte precursors could be attributed to the transferrin fraction of this serum and that human serum transferrin could substitute for guinea pig transferrin as an end-stage maturation factor for guinea pig granulocytes.[3] The data in the present study suggest, however, that GMF activity in human serum is not associated with the main serum transferrin fraction since purified human transferrin alone could not induce human granulocyte precursors to mature in vitro and GMF was well isolated from transferrin when human serum proteins were separated from DEAE-Fractogel displacement chromatography. Our data do show, however, that purified human transferrin potentiates the effect of GMF suggesting that transferrin plays a supporting role in the end-stage maturation of human granulocyte precursor cells in vitro.

The granulocyte maturation factor detected in the present study also appears to be distinct from human granulocyte colony stimulating factor (G-CSF) since the latter could not replace human serum or partially purified GMF as an inducer of end-stage maturation of human granulocyte precursors in vitro. This finding is not unexpected, however, since others have found that normal human serum contains no detectable levels of G-CSF.[12] Furthermore, G-CSF is believed to be primarily a regulator of the proliferation of granulocyte progenitor cells and is dependent in most colony-forming assays on the presence of fetal calf (FCS) serum in the assay medium for the production of colonies containing mature granulocyt[13, 14] and we find that in our maturation assay FCS, like human serum or partially purified GMF, is capable of inducing end-stage maturation of human granulocyte precursors in the absence of added G-CSF (unpublished).

It is interesting to note that end-stage maturation factors also exist for two other major bone marrow cell types, namely, erythrocytes and megakaryocytes, both of which are derived from the same stem cell as granulocytes. Thus, erythropoietin, one of the first of the hematopoietic regulatory proteins to be identified in human serum, serves both as a proliferation regulator and as an end-stage maturation factor for erythrocyte precursor cells.[15] A megakaryocyte maturation factor (MMF) that controls the end-stage maturation of human megakaryocyte precursors in vitro has also been detected in human serum and has been shown to be separate from megakaryocyte colony stimulating factor.[16]

REFERENCES

1. Clark et al: The human hematopoietic colony-stimulating factors. Science, 236:1229 (1987).
2. Evans et al: A new assay for factors that regulate the synthesis of granulocyte differentiation proteins in vitro. J. Cell Physiol., 118:161 (1984).
3. Evans et al: Transferrin induces maturation of neutrophil granulocyte precursors in vitro. Leuk. Res., 10:429 (1986).
4. Evans et al: Concentration of immature and mature granulocytes from normal human bone marrow. Proc. Soc. Exp. Biol. Med., 146:526 (1974).
5. Peterson et al: Ion-exchange displacement chromatography of proteins, using narrow-range carboxymethyldextrans and a new index of affinity. Anal. Biochem., 130:271 (1983).
6. MacGillivray et al: The primary structure of human transferrin. J. Biol. Chem., 258:3543 (1983).
7. Laemmli: Cleavage of structural proteins during assembly of the head of bacteriophage T4. Nature, 227:680 (1970).
8. Lowry et al: Protein measurement with the Folin phenol reagent. J. Biol. Chem., 193:265 (1951).
9. Platzer et al: Human granulocyte colony stimulating factor. Blut, 54:129 (1987).
10. Wachstein M: Alkaline phosphatase activity in normal and abnormal human blood and bone marrow cells. J. Lab. Clin. Med., 31:1 (1946).
11. Wiltshaw et al: Histochemical and biochemical activity. Blood, 10:1120 (1955). Baker et al: Nutritional and regulatory roles human serum in cultures of human granulopoietic cells. Blood, 52:241 (1978).
13. Nicola et al: Purification of a factor inducing differentiation in murine myelomonocytic leukemia cells. J. Biol. Chem., 258:9017 (1983).
14. Nagata et al: Molecular cloning and expression of cDNA for human granulocyte colony-stimulating factor. Nature, 319:415 (1986).
15. Eaves et al: Erythropoiesis in culture. Clin. Haematol, 13:371 (1984).
16. Straneva et al: Separate factors control terminal cytoplasmic maturation of human megakaryocytes. Prog. Clin. Biol. Res., 215:253 (1986).

We claim:

1. Purified inhibitor-free human neutrophilic granulocyte end-stage maturation factor which is substantially free of non-specific proteins, which is distinct from human granulocyte colony stimulating factor, which elutes from a size exclusion HPLC column in the molecular weight range of an albumin standard having a molecular weight of about 65,000 daltons, which binds tightly at pH 7 to a DEAE-Fractogel chromatographic column, which promotes maturation of neutrophilic granulocyte precursors to form end-stage neutrophilic granulocytes, which is capable of inducing human neutrophilic granulocytes to produce alkaline phosphatase, which does not substantially promote proliferation of human granulocyte precursors in a liquid medium, which is inactivated by treatment with protease and wherein the human neutrophilic granulocyte maturation effect can be potentiated by purified human transferrin.

2. A pharmaceutical composition comprising an effective amount of the granulocyte end-stage maturation factor of claim 1, and a non-toxic pharmaceutical carrier.

3. A method for stimulating human neutrophilic end-stage maturation which comprises contacting the maturation factor of claim 1, with human neutrophilic granulocytes.

4. The method of claim 3, which comprises administering the maturation factor to a patient deficient in granulocyte end-stage maturation.

5. The method of claim 4, wherein said maturation factor is administered at a dose of about $5 \times 10^4$ to $3 \times 10^6$ Units per kg of body weight per day.

6. The method of claim 4, wherein said maturation factor is administered intravenously in a non-toxic pharmaceutical carrier.

* * * * *